United States Patent [19]

Howell

[11] 4,407,956

[45] Oct. 4, 1983

[54] CLONED CAULIFLOWER MOSAIC VIRUS DNA AS A PLANT VEHICLE

[75] Inventor: Stephen H. Howell, Del Mar, Calif.

[73] Assignee: The Regents of the University of California, Berkeley, Calif.

[21] Appl. No.: 243,330

[22] Filed: Mar. 13, 1981

[51] Int. Cl.[3] .................. C12N 15/00; C12N 5/00; C12N 1/00

[52] U.S. Cl. .................................. 435/172; 435/240; 435/317; 47/1 R; 47/DIG. 1

[58] Field of Search ............... 435/172, 235, 317, 240

[56] References Cited

PUBLICATIONS

Franck et al., Cell vol. 21, pp. 285–294 (1980).
Shepherd, Ann. Rev. Plant Physiol vol. 30, pp. 405–423 (1979).
Szeto et al., Science vol. 196, pp. 210–212 (1977).
Meagher et al., Vinology vol. 80, pp. 362–375 (1977).
Howell et al., Science vol. 208, pp. 1265–1267 (Jun. 13, 1980).

Primary Examiner—Alvin E. Tanenholtz
Attorney, Agent, or Firm—Bertram I. Rowland

[57] ABSTRACT

Novel methods and compositions are provided for preparing vectors for the introduction of DNA into plant cells for transcription and expression of the DNA. Particularly, cauliflower mosaic virus DNA is inserted into a bacterial cloning vehicle to provide a recombinant plasmid for cloning in a microorganism. The resulting cloned plasmid is genetically manipulated to introduce exogenous or heterologous DNA. Conveniently, linkers can be inserted which provide for a unique restriction site for insertion of exogenous or heterologous DNA. At each stage the modified plasmid may be cloned to provide for relatively large amounts of material for modification and isolation. Besides insertions, deletions may be made, removing non-essential portions of the virus. After completion of the viral modifications, the CaMV is excised from the hybrid plasmid by restriction enzyme cleavage and may be used for systemic infection of plants.

10 Claims, 4 Drawing Figures

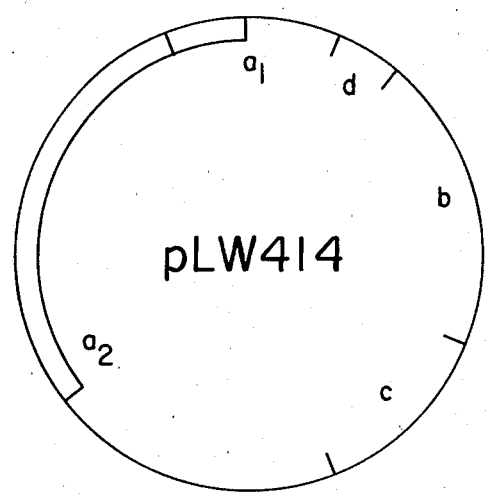
Fig.—1a.
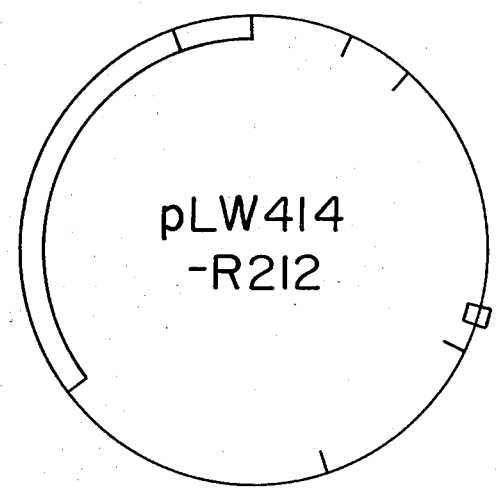
Fig.—1b.
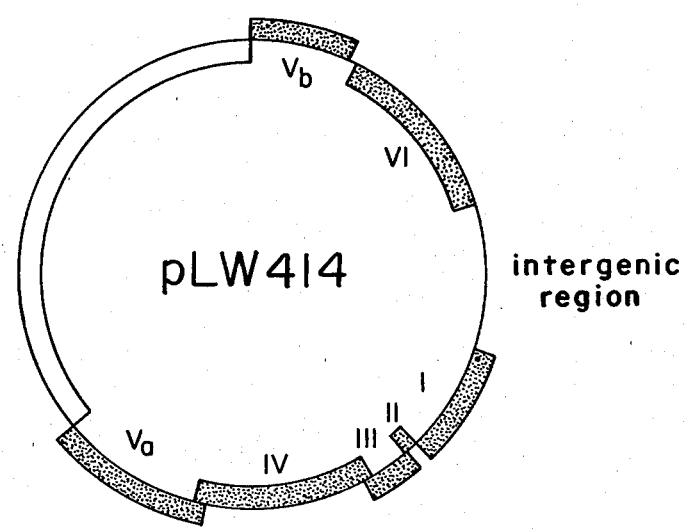
Fig.—1c.

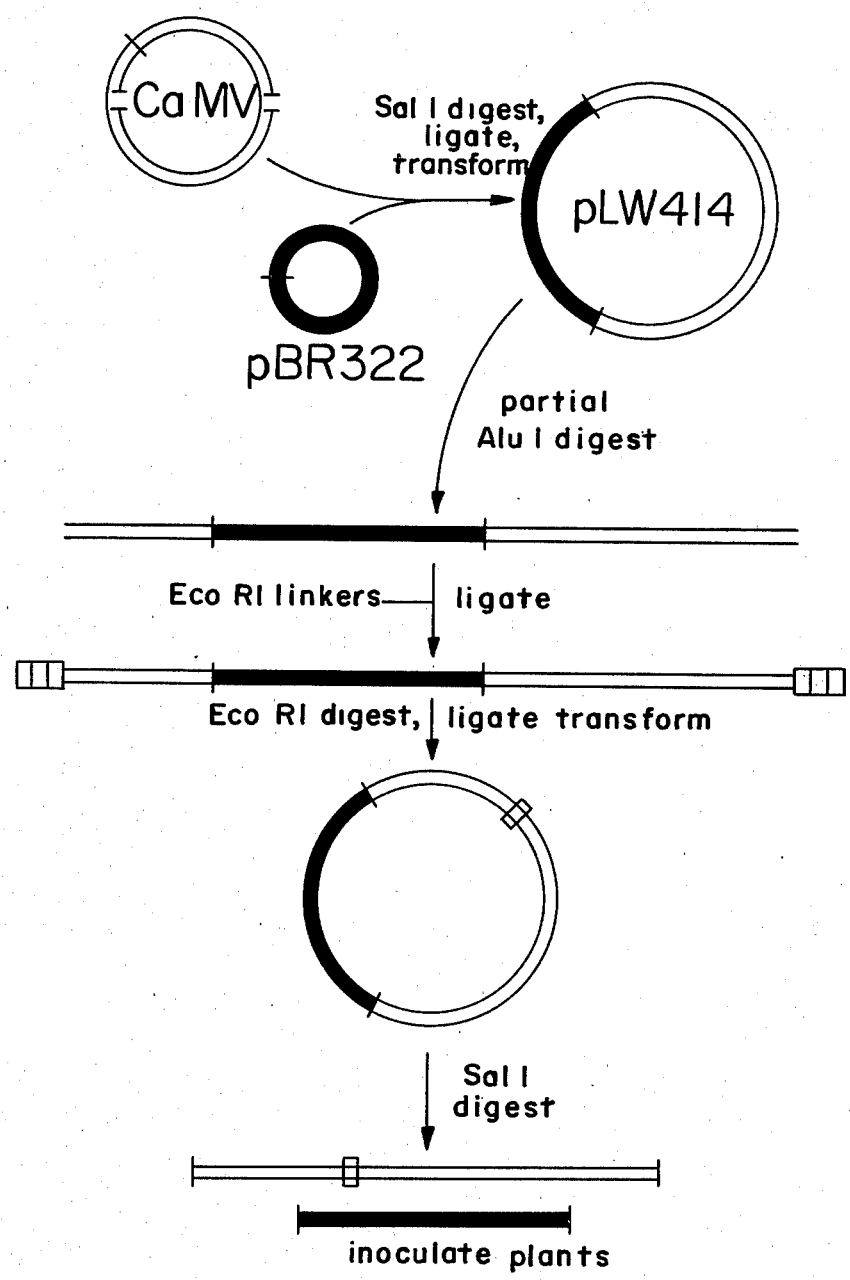
Fig._2

CLONED CAULIFLOWER MOSAIC VIRUS DNA AS A PLANT VEHICLE

The Government has rights in this invention pursuant to Grant No. PCM-7913707 awarded by the National Science Foundation and Grant No. 5901-0410-8-0178-0 awarded by the United States Department of Agriculture.

BACKGROUND OF THE INVENTION

1. Field of the Invention

The genetic modification of higher plants by nontraditional genetic or plant breeding techniques has many possible applications. It may be desirable to modify plants to enhance existing plant properties such as yield, plant growth characteristics, tolerance to stress, disease resistance, etc. It may also be desirable to endow plants with new properties such as the ability to produce non-plant products of possible agricultural or pharmaceutical interest. Genetic and recombinant DNA technology has been successful in permitting the designed modification of certain bacteria (procaryotes) and lower organisms (eucaryotes), such as yeast. As yet, these techniques have not been successfully applied to higher plants for a number of reasons.

First, events which lead to desired genetic modifications in plants are usually infrequent. Microorganisms, unlike plants, can be rapidly multiplied under laboratory conditions allowing for the selection of infrequent genetic modification events. Such selection procedures in plants are, at best, long-term, bulky and expensive and, at worst, are completely undoable in the absence of an appropriate selection system. Second, routes have been found by which exogenous genetic information (DNA) can be readily introduced into many procaryotic microorganisms, but few such routes exist for plants. In many microorganisms, particularly in E. coli and other related bacteria, DNA can be readily introduced by transformation (introduction of DNA by itself) or by transduction (introduction of DNA via a bacteriophage or virus). In general, transformation and transduction procedures have not been described for higher plants. An exception is in the case of the tumor inducing (Ti) plasmid in the bacterium *Agrobacterium*. A portion of the Ti plasmid is transferred from bacterium to plant when *Agrobacterium* infects plants and produces a crown gall tumor. That type of DNA transfer has been recently utilized in certain genetic modification experiments involving plants. Third, much less is known about plant genes and how they operate than is known about the genes of bacteria and certain eucaryotic microorganisms.

The DNA of certain viruses such as cauliflower mosaic virus which infect plants may serve as "vehicles" for the introduction of "exogenous" or "foreign" DNA into plant cells. (The viral DNA is referred to as a "vehicle" and the exogenous or foreign DNA inserted into the vehicle is referred to as "passenger" DNA.) In using viral DNA as a vehicle, there are many considerations. First, if the viral DNA is to be propagated in the host plant in virion form (eventually encapsidated in virus particles), then any adaptation of the viral DNA necessary for the construction of a vehicle must not interfere with infectivity and movement of the virus around the plant, as occurs during the development of a systemic infection. Secondly, the passenger DNA must be inserted in the viral DNA vehicle so that the passenger DNA is stable as the virus multiplies and so that the passenger DNA is replicated and expressed (codes for a desired gene product) in the infected plant. Thirdly, any adaptation of the viral DNA should not prevent the efficient multiplication of the vehicle so that the "passenger" DNA is available in high copy number in infected plant cells.

It is therefore desirable to find ways in which plant viral DNA may be modified, while retaining infectivity, movement and the ability for high multiplication.

2. Description of the Prior Art

Howell et al, Science (1980) 208, 1265–1267 demonstrates the infectivity of cloned cauliflower mosaic virus correcting a previous report by Szeto et al, Science (1977) 196, 210–212 that cloned CaMV lost infectivity. Franck et al, (1980) Cell, 21, 285–294 describes the complete sequence of CaMV. Shalla et al, (1980) Virology 102, 381–388 describes the virus isolates CM1841 and CM4-184.

SUMMARY OF THE INVENTION

Novel methods and compositions are provided for modifying plant viral DNA while retaining infectivity and movement, particularly, cauliflower mosaic virus (CaMV) DNA or an infective fragment capable of movement. The entire viral DNA genome is inserted into a parent bacterial plasmid creating a recombinant DNA molecule (recombinant plasmid) which can be propagated in bacteria. After cloning, the recombinant plasmid is cleaved with restriction enzymes either at random or unique sites in the viral portion of the recombinant plasmid for insertion of foreign, exogenous or heterologous DNA. Particularly, a small oligonucleotide, described as a linker, having a unique restriction site, may be inserted. The modified recombinant plasmid again may be cloned, and further modified by introduction of larger pieces of foreign DNA into the unique restriction site of the linker. The modified viral portion of the recombinant plasmid is then excised from the parent bacterial plasmid and used to inoculate plants. Besides insertion of foreign DNA, the subject method may be accompanied by the deletion of non-essential regions of the viral DNA.

BRIEF DESCRIPTION OF THE DRAWING

FIG. 1 indicates the recombinant plasmid containing the CaMV genome inserted into pBR322, a bacterial plasmid.

( ▭ )

FIG. 1a indicates pLW414 and the EcoRI restriction sites with the partial radial lines, designating the DNA restriction fragments by letters.

FIG. 1b indicates pLW414-R212 derived from pLW414 with the site of the insert of a linker in the intergenic region, repeating the structure of FIG. 1a.

FIG. 1c indicates the open reading frames shown as shaded boxes with Roman numerals (derived from Franck et al. Cell, 21, 285–294, 1980).

FIG. 2 is a flow diagram of a procedure employed in the subject invention for inserting a linker into CaMV DNA.

DESCRIPTION OF THE SPECIFIC EMBODIMENTS

Method and compositions are provided for modifying plant virus DNA. Plant viral DNA is digested with a restriction enzyme at a unique or pseudo-unique site and inserted into an appropriate cloning vehicle (such as a bacterial plasmid) and propagated in a microorganism host. The construction of the recombinant plasmid containing CaMV DNA allows for the production and purification of large amounts of the viral DNA modified in the desired manner. The modified virus may then be excised from the hybrid plasmid at the same sites at which the virus is introduced and the modified virus used to inoculate plants.

The advantage of using a cloned viral DNA as a vehicle to introduce foreign DNA into plants is that a DNA plant virus is a natural vehicle for introducing DNA into a plant. The virus and its DNA have the ability to enter plants, avoid degradation, establish infection and spread throughout the plant. In many instances, attenuated or mild strains of a virus are available which provide for mild infection symptoms, so that the plant remains almost fully productive even though infected by the virus.

For the most part, few DNA plant viruses have been described. This may be because there are a small number of DNA plant viruses, although it is more likely, that there has been no substantial effort in the past to isolate DNA plant viruses. Therefore, exemplary of DNA plant viruses which find use in the subject invention is the cauliflower mosaic virus, abbreviated as CaMV. This virus will infect plants in the plant family Cruciferae. The host range of the virus may be further expanded by appropriate genetic modification.

In referring to foreign DNA, it is intended that the DNA be foreign to the CaMV and not necessarily foreign to the host plant. That is, the DNA is inserted into the CaMV in vitro at some stage, usually a progenitor. In some instances it may be desirable to increase the copy number of a gene endogenous to the plant to enhance the production of the gene product in the plant; to modify the plants' characteristics; or to enhance the production or yield of a product.

In performing the subject invention, CaMV DNA will be inserted into an appropriate bacterial cloning vehicle. For the most part, these techniques are well known, involving the digestion of CaMV DNA and the cloning vehicle with a restriction enzyme. Digestion will normally be at a unique restriction site and conveniently will produce complementary ends, which may be cohesive or sticky ends or blunt ends. In some instances, it may be desirable to modify the ends, by removing bases or adding bases to provide for different restriction sites. Normally, at this point, CaMV DNA will not be modified, only the bacterial cloning vehicle. In some instances one might digest CaMV DNA and the bacterial plasmid DNA each with a different restriction enzyme, followed by modification of the cloning vehicle to provide for complementary ends of the cloning vehicle and linear viral DNA.

A wide variety of cloning vehicles may be employed, that permit the recombinant molecule containing CaMV DNA to be propagated in an appropriate microorganism host such as in bacteria, yeast, etc. Cloning vehicles can be obtained in the form of plasmids, phage, chromosomes, miniplasmids, and the like. The significant fact is that the cloning vehicle allows for the propagation of a large amount of viral DNA in an appropriate microorganism host.

As a matter of convenience, the cloning vehicle should be a substantially different size from the CaMV so as to allow for ease of separation of viral DNA and the cloning vehicle; should not have a restriction site common to the site or sites to be used for insertion of foreign DNA into the viral DNA; and should have a useful restriction site for insertion of the CaMV without destroying the replication function of the cloning vehicle. In addition, it would usually be desirable to have at least one marker or gene in the cloning vehicle which allows for its selection. For the most part, genetic markers will include antibiotic or heavy metal resistance, toxin resistance, phage incompatability, or the like. The choice of genetic marker will normally be one of convenience, rather than necessity. Particularly convenient, is having two markers, where the insertion site for the CaMV inactivates one of the markers, so that one can select for the hybrid DNA plasmid by testing for the respective presence and absence of the two markers.

Various microorganisms can be used as hosts, particularly bacteria, fungi, such as yeast, protozoa, algae and the like. The significant factor is that the host allows for rapid multiplication of the cloning vehicle and isolation of the cloning vehicle.

The preparation of the hybrid DNA plasmid is conventional. Where complementary ends exist, after restriction of the cloning vehicle and the CaMV DNA, the two linear DNA sequences are combined under conditions which allow for annealing of cohesive ends, optionally followed by ligation, or under ligating conditions where blunt ends are involved. Depending upon the cloning vehicle, the host may then be transformed or transfected in accordance with known techniques.

A wide variety of restrictions enzymes, such as Sal I, Sst I, Bst EII, Xho I, Kpn I, Hpa I, etc. are of particular use since CaMV has unique sites for these restriction enzymes.

The transformed host or transformants will then be grown on the appropriate medium to allow for selection of transformants having the desired recombinant DNA plasmid. Selected clones may then be propagated on a larger scale and the recombinant plasmids containing CaMV DNA isolated for further manipulation.

Plasmids may be isolated by density gradient centrifugation, electrophoresis, or other technique which allows for separation of DNA by virtue of molecular weight, composition, or the like. The recombinant plasmid DNA, isolated in this manner, may, but not necessarily, be further modified in adapting the CaMV component of the plasmid to serve as a vehicle in plants. This is usually done by cleaving the recombinant DNA at a restriction site in the viral DNA and inserting, by the same techniques as described above, an adaptive component, a DNA "linker," regulatory component and the like. The insertion of a specific DNA linker, an oligonucleotide of defined sequence containing a specific restriction site, allows one to access this site at a later stage in the procedure and insert larger pieces of foreign DNA.

DNA "linkers" are themselves short bits of foreign DNA usually 8–20 bp in length (depending on the linker). Larger segments of foreign DNA obtained from an appropriate donor to be inserted in the viral DNA region of the recombinant plasmid would range from about 30 bp to a maximum size not yet determined. Most useful structural genes or genetic elements to be inserted into the viral DNA would be about 1000 bp in length, the size of the "coding region" of an average gene. However, genes with coding regions of as small as 30-36 bp could be inserted in the viral DNA vehicle to code in plants for the production of useful polypeptides (small proteins) containing 10-12 amino acid residues. Coding regions to be inserted could be derived from "genomic" DNA obtained directly from the donor source, from other recombinant plasmids derived from genomic DNA of the donor or from copy DNA, cDNA (cloned or not cloned), produced from messenger RNA derived from the donor source. Alternately, the coding region could be wholly or partially synthesized in vitro.

In addition to inserting coding regions of various foreign structural genes into the viral DNA vehicles, foreign DNA may be inserted into the vehicle to serve as a "regulatory element." Regulatory elements would be inserted to insure the appropriate or enhanced "expression" of the foreign structural gene in the infected plant. By the term "expression," it is meant that the foreign gene is transcribed (codes for the synthesis of a desired messenger RNA) and is translated (codes for the synthesis of a desired protein) in the infected plant. Certain regulatory elements are resident in the viral DNA itself. These may be used to express the inserted foreign structural genes, but in the case that resident regulatory elements cannot be used, then other regulatory elements may be inserted. Regulatory elements may be derived from a variety of donors, eucaryotic promoter sites from plants, etc. or the elements may be duplicate copies of elements already resident within the viral DNA. The term, regulatory element, is also taken to include coding signals—signals for transcription initiation and termination, capping sites, ribosome binding, translation initiation start and stop signals, etc.

A wide variety of genes are of interest for insertion into the virus, particularly, genes which modify the existing properties of the plant or endow the plant with the ability to produce new substances. Foreign genes can provide for enhanced production of protein, greater tolerance to environmental stresses, improved qualities in fruit and vegetable products, novel ornamental plants, production of compounds of physiological and pharmaceutical interest compounds, either proteinaceous, or non-proteinaceous, resistance to pests and pesticides, nitrogen fixation, either independently or through symbiosis, or the like. The various genes may be introduced simultaneously with or sequentially with regulatory signals as described above.

It is essential that the site in the viral DNA vehicle at which the foreign DNA is introduced does not destroy infectivity of the viral DNA and its movement throughout the plant. Therefore, the subject method allows for introducing the foreign DNA at a variety of restriction sites, either unique or pseudo-unique, cloning the product and determining whether the essential characteristics of the virus have been retained. In this manner, one can rapidly isolate a relatively large amount of modified virus which can be screened for infectivity and movement.

One or another site in the virus may be preferred. Particularly, some sites in the virus are found to be more active in expression than other sites. It would be expected that by inserting foreign DNA into an active site, one would anticipate enhanced expression of the foreign DNA. The ability to obtain useful amounts of modified hybrid DNA plasmid permits the screening of a plurality of hybrid DNA plasmids differing in the site of insertion.

Besides insertions, there will be situations where compensatory deletion of viral DNA segments are also desirable. Since the nucleotide sequence of the virus has been determined, various non-essential portions of the virus may be removed. This may become important where relatively large insertions are involved which might interfere with propagation in the plant of viral DNA in virion form.

After the viral portion of the hybrid DNA plasmid has been modified, the modified virus may be excised from the hybrid DNA plasmid and may be used to inoculate plants directly in linear form or ligated in circles or concatamers. Depending upon the nature of the original virus, various techniques may be employed for infecting plant cells. Young leaves may be mildly abraded and then contacted with the viral DNA. After infection, the viral DNA may be transmitted by aphids, where the aphid transmissible gene is operative. Mechanical techniques can also be employed. The manner of infection is not critical to this invention, any method presently known or developed in the future may be employed. Alternatively tissues or single cells may be infected.

After infection, the plant cells, plant or plantlet may be grown in conventional ways. Depending upon the nature of the DNA, where a gene has been introduced for production of a valuable product, the product will then be isolated by known techniques. Various extraction, chromatographic, or other means may be used.

The following examples are offered by way of illustration and not by way of limitation.

EXPERIMENTAL

The entire CaMV genome was obtained from viral isolate CM4-184 (Lung and Pirone, Phytopathology 62, 910 (1973)). The strain is not aphid transmissible. The DNA was cut at the single Sal I site and inserted into the Sal I site of pBR322. Clones were obtained representing the insertion of CaMV DNA in the plasmid in both orientations (Howell et al., Science (1980) 208, 1265-1267). DNA from the viral isolate CM4-184 has two site-specific single-strand breaks, one in each strand and nearly opposite each other across the CaMV DNA circle. These breaks were sealed during cloning as evidenced by the fact that the recombinant plasmids carrying CaMV DNA behaved on CsCl-ethidium bromide density gradients as covalently closed circular DNA forming a single band at about 1.59 g/cm$^3$. The hybrid DNA plasmid was then cloned in the bacterial vector E. coli C600. After growth of the host in a conventional nutrient medium, the cells were lysed and the hybrid DNA plasmid isolated in accordance with conventional techniques (Kahn et al., Methods in Enzymology 68, 268-280 (1979)). The hybrid DNA plasmids pLW408 and pLW414 (indicating the alternative orientations) were Sal I-digested and the digested product used for infecting turnip plants (Brassica rapa L., cultivar Just Right). An inoculum (50 μl) containing 20 micrograms DNA in 150 mM NaCl, 15 mM sodium citrate and 2 mg of Celite 545 (an abrasive) was employed. The inoculum was rubbed on the leaves of two or three 2-week-old turnip plants. Plants were scored for the appearance of symptoms four to five weeks after infection. The Sal I digested hybrid DNA plasmids (digestion of three hours with 0.5 enzyme unit per microgram of DNA) infected all the plants tested.

DNA linkers (Rothstein et al., Methods in Enzymology 68, 98–109 (1979)) were inserted into pLW414 by a procedure-modified from Heffron et al., Proc. Nat. Acad. Sci. 75 6012–6016 (1978) as shown in FIG. 2. The hybrid plasmid pLW414 was digested with the restriction enzyme Alu I at 46° C. for two hours in the presence of 80 μg/ml ethidium bromide to produce a high proportion (approximately 30%) of full-length linear molecules. Linear molecules were selected from DNA forms separated by sedimentation on a 5–20% sucrose gradient. Linear molecules were methylated with Eco R1 methylase to protect existing sites from subsequent digestion with Eco RI (Heffron et al., Proc. Nat. Acad. Sci. 75, 6012–6016, 1978). Eco RI linkers, d(GGAATTCC) in a 500 molar end-group excess were blunt end ligated to linear pLW414. DNA with attached linkers was digested with Eco RI yielding plasmid molecules with attached monomeric linkers and "sticky ends". Such molecules were circularized with T4 DNA ligase and used to transform E. coli C600 (Kahn et al., Methods in Enzymology 68, 268–280 (1979). Appropriate clones were selected after examining Eco RI digest of small scale preparations of the cloned DNA.

One linker insertion at an Alu I site near a Bgl I site between region I and region VI described as an intergenic region was found to retain infectivity, being in the Eco RI b restriction fragment adjacent to the Eco RI c restriction fragment. See rectangle in FIG. 1B.

To inoculate plants, 20 micrograms of the cloned, modified plasmid DNA was digested with Sal I, the digest extracted with phenol, ethanol precipitated and dissolved in the inoculum described above. The plants were infected as previously described and scored as described above. The virus was found to be infective.

In accordance with the subject invention, a novel method is provided for modifying plant viruses by inserting foreign DNA into the viral genome. The method permits modification of the viral DNA under conditions where various modifications can be screened for retention of infectivity and movement. In addition, one can obtain large amounts of the modified viral DNA for use in infecting plants. In addition, modified CaMV DNA has been prepared with insertion of an oligonucleotide into an active region, with retention of infectivity and movement of the product. The oligonucleotide insertion provides a unique restriction site which can be used for introduction of additional DNA, either regulatory or structural genes.

Although the foregoing invention has been described in some detail by way of illustration and example for purposes of clarity of understanding, it will be obvious that certain changes and modifications may be practiced within the scope of the appended claims.

What is claimed is:

1. A method for modifying Cauliflower mosaic viral DNA while maintaining the capability of movement, said movement capability comprising replication and systemic infection, which comprises:
    combining linear cauliflower mosaic viral DNA with a bacterial cloning vehicle permitting propagation of the resulting hybrid DNA plasmids in an appropriate microorganism host;
    cloning said hybrid DNA plasmids in said microorganism to provide a source of said hybrid DNA plasmid;
    inserting foreign DNA into said cloned hybrid DNA plasmids at the intergenic region between reading frames VI and I of said Cauliflower mosaic viral DNA to provide a modified Cauliflower mosaic hybrid DNA plasmid containing modified viral DNA, where said intergenic region is non-essential to propagation and movement of said viral DNA;
    cloning said modified hybrid DNA plasmids in a microorganism host; and
    excising said modified Cauliflower mosaic viral DNA from said hybrid DNA plasmid to provide a plant virus capable of propagation and movement.

2. A method according to claim 1, wherein said cauliflower mosaic virus is an attenuated or mild strain.

3. A method according to claim 1, wherein said site is an Alu I restriction site at or near a Bgl I restriction site.

4. A method according to any of claims 1, wherein said foreign DNA is an oligonucleotide linker of at least 8 bp.

5. A method according to claims 1, wherein said cloning vector has at least 1 marker for selection.

6. A method according to claims 1, wherein said cloning vector has at least 2 markers for selection, wherein said viral DNA is inserted into one of said markers.

7. Recombinant Cauliflower mosaic virus capable of propagation and movement, said movement comprising replication and systemic infection, said virus or a parent thereof having received in vitro an insertion of foreign DNA at the intergenic region between reading frames VI and I, a site non-essential to such movement.

8. Cauliflower mosaic virus according to claim 7, wherein said insertion is an oligonucleotide of at least 8 bp.

9. Cauliflower mosaic virus according to claim 7 or 8, wherein said insertion is an Alu I site at or near a Bgl I restriction site.

10. A plant cell from the family Cruciferae containing at least one cauliflower mosaic virus according to any of claims 7 or 8.

* * * * *